(12) United States Patent
Obrebski et al.

(10) Patent No.: US 7,190,513 B2
(45) Date of Patent: Mar. 13, 2007

(54) MICROSCOPY SYSTEM AND METHOD

(75) Inventors: Andreas Obrebski, Düesseldorf (DE); Christoph Hauger, Aalen (DE); Michael Haisch, Aalen (DE); Fritz Straehle, Heubach (DE)

(73) Assignee: Carl Zeiss AG, Oberkochen (DE)

( * ) Notice: Subject to any disclaimer, the term of this patent is extended or adjusted under 35 U.S.C. 154(b) by 86 days.

(21) Appl. No.: 10/910,730

(22) Filed: Aug. 3, 2004

(65) Prior Publication Data

US 2005/0063047 A1 Mar. 24, 2005

(30) Foreign Application Priority Data

Aug. 4, 2003 (DE) ................. 103 35 644

(51) Int. Cl.
*G02B 21/22* (2006.01)
*G02B 21/00* (2006.01)

(52) U.S. Cl. ...................... 359/376; 359/384

(58) Field of Classification Search ................ 359/384, 359/372, 375, 376, 382, 393, 374, 377, 368; 250/203.1, 203.2
See application file for complete search history.

(56) References Cited

U.S. PATENT DOCUMENTS

| | | | |
|---|---|---|---|
| 3,824,022 A | 7/1974 | Mancino | |
| 3,887,267 A | 6/1975 | Heller | |
| 4,881,709 A | 11/1989 | Nakamura | |
| 5,067,804 A | 11/1991 | Kitajima et al. | |
| 5,074,651 A * | 12/1991 | Nagamine | 359/384 |
| 5,332,181 A | 7/1994 | Schweizer et al. | |
| 5,345,087 A | 9/1994 | Luber et al. | |
| 5,481,111 A | 1/1996 | Rosar et al. | |
| 5,657,128 A * | 8/1997 | Muller et al. | 356/612 |
| 5,769,441 A | 6/1998 | Namngani | |
| 5,836,416 A | 11/1998 | Muller et al. | |
| 5,867,210 A | 2/1999 | Rod | |
| 5,867,308 A | 2/1999 | Pensel et al. | |
| 5,982,532 A * | 11/1999 | Mittelstadt et al. | 359/368 |
| 6,005,710 A | 12/1999 | Pensel et al. | |
| 6,046,844 A | 4/2000 | Duis | |
| 6,133,945 A | 10/2000 | Stuettler | |
| 6,317,260 B1 | 11/2001 | Ito | |
| 6,452,625 B1 | 9/2002 | Kapitza | |
| 6,525,878 B1 * | 2/2003 | Takahashi | 359/466 |
| 2003/0151810 A1 | 8/2003 | Haisch et al. | |
| 2004/0017607 A1 | 1/2004 | Hauger et al. | |
| 2004/0036962 A1 | 2/2004 | Brunner et al. | |

FOREIGN PATENT DOCUMENTS

CA 1002356 12/1976

(Continued)

*Primary Examiner*—Alessandro Amari
(74) *Attorney, Agent, or Firm*—Potomac Patent Group PLLC

(57) ABSTRACT

A microscopy system and method provides functionalities for a user which are controllable by the user by displacing a body portion of the user. The functionalities comprise displacing a portion of a support mounting the microscopy optics and adjusting a stereo base for generating stereoscopic representations of an object.

33 Claims, 6 Drawing Sheets

FOREIGN PATENT DOCUMENTS

| | | |
|---|---|---|
| DE | 2418565 | 1/1975 |
| DE | 4202505 A1 | 8/1993 |
| DE | 4202922 A1 | 8/1993 |
| DE | 4213312 A1 | 10/1993 |
| DE | 4317522 A1 | 11/1993 |
| DE | 19635666 C1 | 12/1997 |
| DE | 10203215 A1 | 8/2003 |
| EP | 0293228 B1 | 11/1988 |
| EP | 0788613 B1 | 8/1997 |
| EP | 1333305 A2 | 8/2003 |
| EP | 1333306 A2 | 8/2003 |
| WO | WO 96/06507 | 2/1996 |

\* cited by examiner

MICROSCOPY SYSTEM AND METHOD

This application claims the benefit of priority application DE 103 35 644.4 filed in Germany on Aug. 4, 2003. The subject matter of this application is incorporated herein by reference.

BACKGROUND OF THE INVENTION

Field of the Invention

The present invention relates to a microscopy system and method for presenting an image of an object to one or plural users. The invention further relates to a microscopy system and method of generating stereoscopic images of an object for one or plural users.

A conventional microscopy system comprises a microscopy optics having an objective arrangement including an objective arrangement, and a pair of oculars, and a mount having plural mounting members which are displaceable relative to each other. One of the mounting members carries the microscopy optics such that the microscopy optics is displaceable in space and may be positioned by a user relative to an object to be inspected. For this purpose, the user grasps with their hand one of the mounting members or a portion or chassis of the objective arrangement to move the objective arrangement to a desired position relative to the object. However, if the user has to perform manipulations with working tools in both hands, they will have to release the tool from their hand to displace the objective arrangement with their hand with the intention to inspect the object from a different perspective, direction or view point. Only after displacing the objective arrangement with their hand can the tool be grasped again to continue their task.

It appears that the procedure illustrated above of changing the perspective and view point of the microscopy optics is troublesome. An improvement to this problem is suggested in U.S. Pat. No. 5,345,087. According to this suggestion, a measuring system is mounted on the microscopy optics for measuring a position of the microscopy optics relative to the head of the user. The measuring system further controls actuators of the head to perform movements such that the microscopy optics is permanently maintained in a position relative to the mount of the user such that the user is permanently able to look into the oculars of the microscopy optics. If the user moves their head, the microscopy optics will follow such movements automatically. This has the result that the microscopy optics is sort of fixedly connected to the head of the user.

If the user now wants to turn their view away from the oculars for a short moment to have, for example, a direct view onto the object or onto an adjacent portion of the table to pick up a further tool, this will be impossible with the conventional system. Since the microscopy optics continuously follows every movement of the head of the user, the user will finally not be able to avoid looking through the oculars and to look by the side of the oculars to the table. This is the reason why the suggested system was not successful in practise.

SUMMARY OF THE PRESENT INVENTION

The present invention has been accomplished taking the above problems into consideration.

It is an object of the present invention to provide a microscopy system and method allowing a user to readily change a position of the microscopy optics relative to the object.

It is a further object of the invention to provide a microscopy system and method allowing sufficient freedom of movement to the head of the user such that the user may turn their view away from the microscopy optics.

It is a further object of the invention to provide a microscopy system and method suitable to providing representations of the object to one or plural user.

It is a further object of the invention to provide a microscopy system and method allowing to change a stereo base of a stereoscopic representation of the object.

The invention provides a microscopy system and method for presenting a representation of an image of an object for inspection by at least one user. A microscopy system to which the invention is applicable may comprise a microscopy optics having an objective arrangement for imaging an object which may be disposed in an object plane of the objective arrangement, and a visualizing unit for presenting an image of the object to the user; a first support for supporting at least the objective arrangement of the microscopy optics in a region close to the object to be inspected, wherein the first support comprises at least one actuator for displacing the objective arrangement relative to the object to be inspected; a first position sensitive unit configured to detect a position of a body portion of the user relative to a predetermined first location; and a control system comprising a first control portion configured to control the at least one actuator of the first support with respect to a displacement of the objective arrangement in dependence of a displacement of the head of the user.

The visualizing unit may comprise, for example, two oculars, such as a binocular, which is mounted on the objective arrangement. Further, it is also possible that the visualizing unit is independent from the objective arrangement and may be freely displaced thereto, and the visualizing unit may comprise a display carried by the head of the user, such as a head mounted display. Such visualizing unit is supplied with image data representing the image to be displayed. The image data may be generated by a camera associated with the objective arrangement and may be supplied to the display unit via a cable or a wireless connection.

The microscopy system may also comprise plural visualizing units for supplying representations of the object obtained by one common objective arrangement to plural users.

According to a first aspect of the invention the microscopy system comprises an activation signal receiver for generating an activation signal upon a corresponding action of the user, the activation signal receiver being operable and may be activated by the user, and wherein the first portion of the control system is configured to control the at least one actuator of the first support in view of the displacement of the objective arrangement only if the activation signal is received by the activation signal receiver.

Using such a system, the user may indicate to the microscopy system that a movement of their head is performed with the intention to displace the objective arrangement of the microscopy optics relative to the object or that the head is moved for some other reason which should not result in a displacement of the objective arrangement. In particular, involuntary displacements of the users head which are caused by, for example, breathing, or changing a position of a leg of the user, will not result in a displacement of the objective arrangement. In addition, further users of the microscopy system who are also supplied with representations of the image of the object generated by the objective arrangement will not perceive a permanently shaking image.

The activation signal may be supplied to the activation signal receiver of the microscopy system in various ways. For example, a switch may be used to receive the activation signal. The switch may comprise a switch disposed on a floor and be operable with a foot of the user, or the switch may comprise a mouth switch which is operated by the mouth of the user, and example of which is known from U.S. Pat. No. 3,887,267. Further, the activation signal may be supplied as an acoustic signal generated by the user as a spoken word, a whistle or other. In such a situation an embodiment of the microscopy system may comprise a microphone, and the control system comprises a second portion for analysing a sound received by the microphone to decide whether the received sound comprises the activation signal.

The actuators of the first support will be controlled in view of displacing the objective arrangement based on a displacement of the body portion of the user only if the microscopy system receives the activation signal.

Within the context of the present application, the displacement of items such as the body portion of the user comprises a lateral or translational displacement relative to a location and a rotational or angular displacement relative to a location.

Thus, a lateral displacement of the head of the user may result in a lateral displacement of the objective arrangement relative to the objective plane of the objective arrangement. Further, a rotation of the head of the user about it's horizontal or vertical axis may result in a corresponding rotation of the objective arrangement relative to it's horizontal or vertical axis or about an axis which is aligned with the objective plane or orthogonally orientated to the objective plane.

It is further possible that, upon receipt of the activation signal, a further function of the microscopy system is controlled in dependence of the movement of the body portion of the user. Such other function, different from a displacement of the objective arrangement, may comprise a change of a magnification of a zoom system of the microscopy system, or other. For example a movement of the head of a user in a direction towards the object may increase the magnification. According to an embodiment of the invention, the microscopy system may be switched between various modes of operation in which movements of the head may selectively control various functions of the microscopy system.

According to a second aspect of the invention, the microscopy system is configured such that an amount of the displacement of the objective arrangement is dependent on an amount of the displacement of a body portion of the user or of a visualization unit. Thus, a small displacement of the body portion or visualization unit will result in only a small displacement of the objective arrangement, whereas a larger displacement of the body portion or visualization unit will result in a corresponding larger displacement of the objective. According to an embodiment of the invention, the amount of displacement of the objective arrangement is smaller than the amount of the displacement of the body portion or visualization unit. This embodiment in based on the consideration that the visualizing unit provides a magnified image of the object to the user. If it assumed that the magnification is 5× and the amount of displacement of the objective arrangement is equal to the amount of displacement of the head of the user, a lateral displacement of the head by such as 1 cm, the objective arrangement will also be displaced by 1 cm. Such displacement of the objective arrangement will appear to the user, when viewed in the visualizing unit, as a displacement of the object by 5 cm. If the user desires to displace the objective by an amount of only 1 mm it will be difficult for the user to perform corresponding small displacements with their head. This applies in particular for large magnifications of the microscopy systems. In such situations, it is a particular advantage to provide a reduction of the amount of displacement of the objective arrangement which are performed in dependence on amounts of displacement of the head of the user. According to an exemplary embodiment of the invention, such a reduction is dependant on a setting of the magnification of a zoom system of the microscopy optics. The zoom system may comprise any magnification changing function of an optical or digital zoom.

According to an exemplary embodiment of the invention, the visualizing unit is mounted on a second support to be displaceable relative to the objective arrangement. Compared to a situation where the visualizing unit, such as a binocular, is fixedly mounted relative to the objective arrangement, the user will not be forced to take an uncomfortable position for perceiving the image of the object from a particular desired viewpoint, since the visualizing unit may be displaced relative to the objective arrangement. Further, compared to a situation where the visualizing unit is provided as a head mounted display, the mounting of the visualizing unit on the second support allows the user to easily move their head away from the visualizing unit to directly view the object if this is necessary, or to directly view a tool which is to be grasped and which is disposed on an object table.

According to an exemplary embodiment, the second support for mounting the visualizing unit is mounted on one of the support members of the second support supporting the objective arrangement.

According to an exemplary embodiment, plural second supports are provided for each mounting a separate visualizing unit associated with one of plural users.

According to an exemplary embodiment, the second support is configured to mount the visualizing unit such that the visualizing unit may be pivoted about a vertical axis extending close to the objective arrangement.

According to a further exemplary embodiment, the first support comprises at least one actuator for displacing the objective arrangement relative to the inspected object under the control of a control system. Herein, a displacement of the visualizing unit which may be caused by the user is detected, and the at least one actuator of the first support is controlled to displace the objective arrangement in dependence of the detected displacement of the visualizing unit. According to an embodiment it is possible that a translational displacement of the visualizing unit will result in a translational displacement of the objective arrangement, or that a rotational displacement of the visualizing unit about one or the other axis will result in a corresponding rotation of the objective arrangement. Again, an amount and/or a direction of the displacement of the objective arrangement may correspond to an amount and/or direction of displacement of the visualizing unit.

According to a further embodiment herein, a reduction of amounts is provided such that an amount of displacement of the objective arrangement is smaller than the corresponding amount of displacement of the visualizing unit.

According to a further embodiment of the invention, a switching unit is provided on the second support, wherein the switching unit is operated by the user using their hand to generate control signals for controlling the at least one actuator of the first support for displacing the objective arrangement in dependence of the user operating the switching unit. The switching unit may be disposed close to the visualizing unit on the second support.

Under a further aspect of the present invention, there is provided a method and system for generating pairs of stereoscopic representations representing two images of the object generated by the microscopy optics from different viewpoints or viewing directions, respectively. The two representations are presented to both eyes of the user such that they perceive a stereoscopic impression of the object. The two viewing directions may be adjusted by the microscopy system within a certain range and should be adjusted by the system such that the user, when viewing the two representations of the object, perceives a realistic impression of the object.

One approach for achieving such a purpose comprises determining the two viewing directions in dependence of a circumferential position of the user about a fixed point associated with the objective arrangement of the microscopy optics. However, such an approach has not proved to be completely successful in practise.

According to a further aspect of the invention, the viewing directions are adjusted in dependence of an orientation of a portion of the body of the user and/or an orientation of a visualizing unit for displaying the representations. According to an embodiment of the invention, the method comprises using a microscopy objective arrangement having a main axis and an objective plane orientated transversely to the main axis, and having two beam paths. Main central rays of the two beam paths intersect with the object plane at substantially a common location, and the main central rays are substantially disposed in a common first plane. The two main central rays define the viewing directions of the generated representations, as illustrated above. An orientation of the first plane about the main axis of the objective arrangement is adjusted in dependence of a detected orientation of a portion of the body of a user, and/or in dependence of an orientation of a pair of displays viewed by the user.

According to an exemplary embodiment of the invention, the first plane is permanently orientated such that it is parallel to the orientation of the body portion of the user or to the pair of displays, permanently following changes of these orientations. According to further embodiments, an offset angle is provided between the orientation of the first plane and the orientation of the body portion of the user and the two displays, respectively. Such offset angle may be adjustable by the user, or may be automatically controlled.

According to an exemplary embodiment, the orientation of the body portion of the user is the users shoulder, and the first plane may be determined such that it is parallel to a line connecting the left and right shoulders of the user, wherein and offset angle may be provided between the connecting line of the left and right shoulders and the orientation of the first plane. According to another exemplary embodiment, the body portion chosen is the head of the user, and the first plane is oriented in dependence on the orientation of the head of the user.

According to a further exemplary embodiment the orientation of the display unit is detected for determining the orientation of the first plane, and the first plane is adjusted to be parallel to a line connecting the left and right display. Also, in such embodiment and offset angle may be provided between the orientation of the first plane and the orientation of the connecting line.

According to an exemplary embodiment, the two representations of the object are generated from a data model of the object, wherein the data model is obtained by a topology detecting unit of the microscopy system. The two representations of the object obtained from the data model will then represent the object from two different viewing directions which substantially intersect with each other at a common location and which are substantially disposed in a common first plane. The first plane is rotated about a main axis of the topology detecting unit in dependence of a detected orientation of the body portion of the user and the pair of displays, respectively. Again, various body portions of the user may be used for determining the orientation of the first plane and offset angles may be provided as illustrated above.

BRIEF DESCRIPTION OF THE DRAWINGS

The forgoing as well as other advantageous features of the invention will be more apparent from the following detailed description of exemplary embodiments of the invention with reference to the accompanying drawings, wherein.

DETAILED DESCRIPTION OF EXEMPLARY EMBODIMENTS

Figure 1:
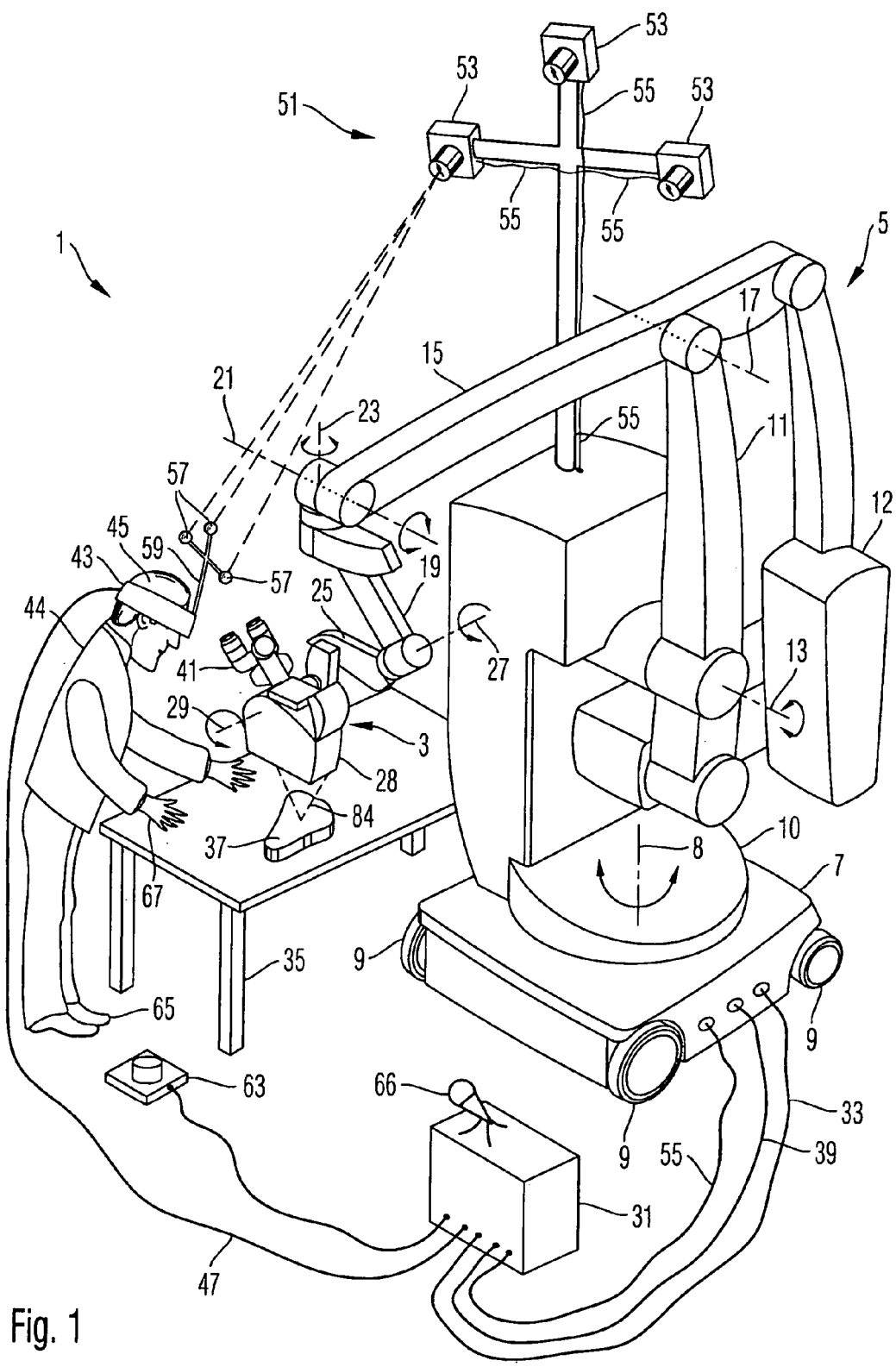
FIG. 1 is a perspective illustration of an embodiment of a microscopy system having a support controlled in dependence of a displacement of the head of a user.

In the exemplary embodiments described below, components that are alike in function and structure are designated as far as possible by alike reference numerals. Therefore, to understand the features of the individual components of a specific embodiment, the descriptions of other embodiments and of the summary of the invention should be referred to.

An embodiment of a microscopy system and method is schematically in FIG. 1. A microscopy system 1 shown in FIG. 1 comprises a microscopy optics 3 mounted on a support 5 such that it is displacable in space. The support 5 comprises a plurality of support members which are displacable relative to each other. A base member of the support 1 has wheels 9 and is disposed on a floor of a room. The base member 7 carries a support member 10 which is rotatable relative to the base 7 about a vertical axis 8. The support member 10 carries a support arm 11 mounted on the support member 10 to be pivotable about a horizontal axis 13. The support arm 11 carries a further support arm 15 to be pivotable about a horizontal axis 17. The support arm 15 carries an intermediate support member 19 which is pivotable relative to the support arm 15 about a horizontal axis 21 and a vertical axis 23. The intermediate support member 19 carries a further intermediate support member 25 to be pivotable about a diagonal axis 27. The intermediate support member 25 carries a chassis 28 of an objective arrangement of the microscopy optics 3 to be pivotable about an axis 29.

Each of the axis 8, 13, 17, 21, 23, 27 and 29 has associated therewith a actuator (not shown in FIG. 1) driven by a motor to displace the members 7, 10, 11, 15, 19, 25 and 28 relative to each other. A controller 31 which may be embodied as a general purpose computer, is connected with the various motors through a control cable 33.

A balancing weight 12 is provided for reducing an actuating force to be generated by the actuators associated with the axis 13 and 17.

The microscopy optics 3 comprises an objective arrangement such as an objective lens (not shown in FIG. 1) which is contained in the chassis 28 and which generates stereoscopic images of an object 37 disposed on an object table 35. The images detected by the objective arrangement are supplied to the controller 31 as digital data through a data cable 39.

The microscopy optics 3 further comprise a pair of oculars 41 which the user may use to perceive a stereoscopic representation of the object 37. The oculars 41 and the objective arrangement may have a common optical beam path, or the oculars may comprise displays, such as LCD displays, for displaying image data detected through the objective arrangement by, for example, cameras. The oculars 41 are, however, only optionally provided as an alternative or additional visualizing unit for a head mounted display 43 which the user 44 carries on their head 45. The head mounted display 43 comprises two displays supplied with image data from the controller 33 via a data cable 47. The two displays of the head mounted unit display a representation of the object 37 such that the user may perceive a stereoscopic representation of the object 37. The user may freely move relative to the object 37 and may permanently perceive the representation of the object during their movement. Thus, the user is not limited to a position of the oculars 41 when choosing their own position for inspecting the object 37.

The microscopy system 1 further comprises a position detector 51 for detecting a position of the head 45 of the user 44, relative to the support member 10 of the support 5. The position detector 51 comprises three cameras 53 which are disposed at a distance from each other and not on a common line. Images of the cameras 53 are supplied to the controller 31 via a data cable 55. The position detector 51 further comprises three light emitting diodes 57 which are disposed at a distance from each other and not on a common line and which are carried by the user 44 on their head 45. The light emitting diodes are mounted on mounting rods 59 which are fixed to the head mounted display 43 which is fixed to the head 45 of the user. It appears that there are other possibilities to fix the light emitting diodes 57 or other suitable elements to the head 45 or any other body portion of the user 44.

The controller 31 analyses the images generated by the cameras 53 to determine the positions of the light emitting diodes 57 and to further calculate the position of the head 45 of the user relative to the support member 10. The position of the head is determined both with respect to the orientation of the head and the location of the head. Since the controller 31 also controls the actuators of the support 5, the controller 31 also has the necessary information to determine a position of the objective arrangement, both with respect to a location and orientation thereof. Thus, the controller 31 may calculate the position of the head 45 relative to the objective arrangement or the object 37. It is also possible that an additional three light emitting diodes are mounted on the chassis 28 of the microscopic optics 3 such that the position of the objective arrangement may be determined by the controller 31 by analysing the images detected by the cameras 53.

The microscopy system 1 further comprises a foot switch 63 which is connected to the controller 31 via a cable 61 and which is disposed on the floor to be operated with a foot 65 of the user 44. Operation of the foot switch 63 activates the controller 31 to control the actuators of the support 5 in dependence of a displacement of the head 45 of the user 44 detected by the position detector 51. For example, a translational displacement of the head 45 is transformed to a corresponding parallel displacement of the chassis 28 of the microscopy optics 3, wherein an amount of displacement of the chassis 28 is reduced relative to the amount of displacement of the head 45. Such reduction of amounts is based on an adjusted magnification of the objective arrangement. If, for example, the magnification is 8×, a displacement of the head 45 by 1 cm will result in a displacement of the objective arrangement by 0.125 mm. In other embodiments it is possible to choose other reductions of amounts, however. Similarly, a rotation of the head 45 of the user about a certain axis in space will result in a corresponding rotation of the chassis 28 about an axis which is parallel to the axis of rotation of the head 45. In one particular embodiment, the amount of rotation of the chassis is equal to the amount of rotation of the head of the user, and in other embodiments, the amount of rotation of the chassis may be reduced as compared to the amount of rotation of the head of the user.

By using the microscopy system 1, the user may freely move their head relative to the object 37 while permanently perceiving the representation of the object 37, and further, the user may operate the foot switch 63 to use an intentional movement of their head 45 for displacing the objective arrangement relative to the object 37.

As an alternative or in addition to the foot switch 63, a microphone 66 is provided as an activation signal receiver to allow the controller 31 to displace the objective arrangement in dependence on displacement of the head of the user. The microphone receives speech signals emitted by the user and which are analysed by the controller 31 to determine whether the user has emitted a predetermined speech signal for controlling the support 5 in dependence on the movements of the user, and whether a second predefined signal was emitted to stop such control of the support such that the user may again move freely about the object 37 without displacing the objective arrangement.

According to an alternative embodiment is it possible that the position detector 51 detects a position of any other body portion of the user 45, such as a hand 67 rather than the position of the head 45. For this purpose three light emitting diodes may be carried by the hand 67 of the user. According to further embodiments the position detector 51 is not implemented to comprise three cameras 53 and three light emitting diodes and may operate according to any other principle which might even be conventional.

Figure 2:
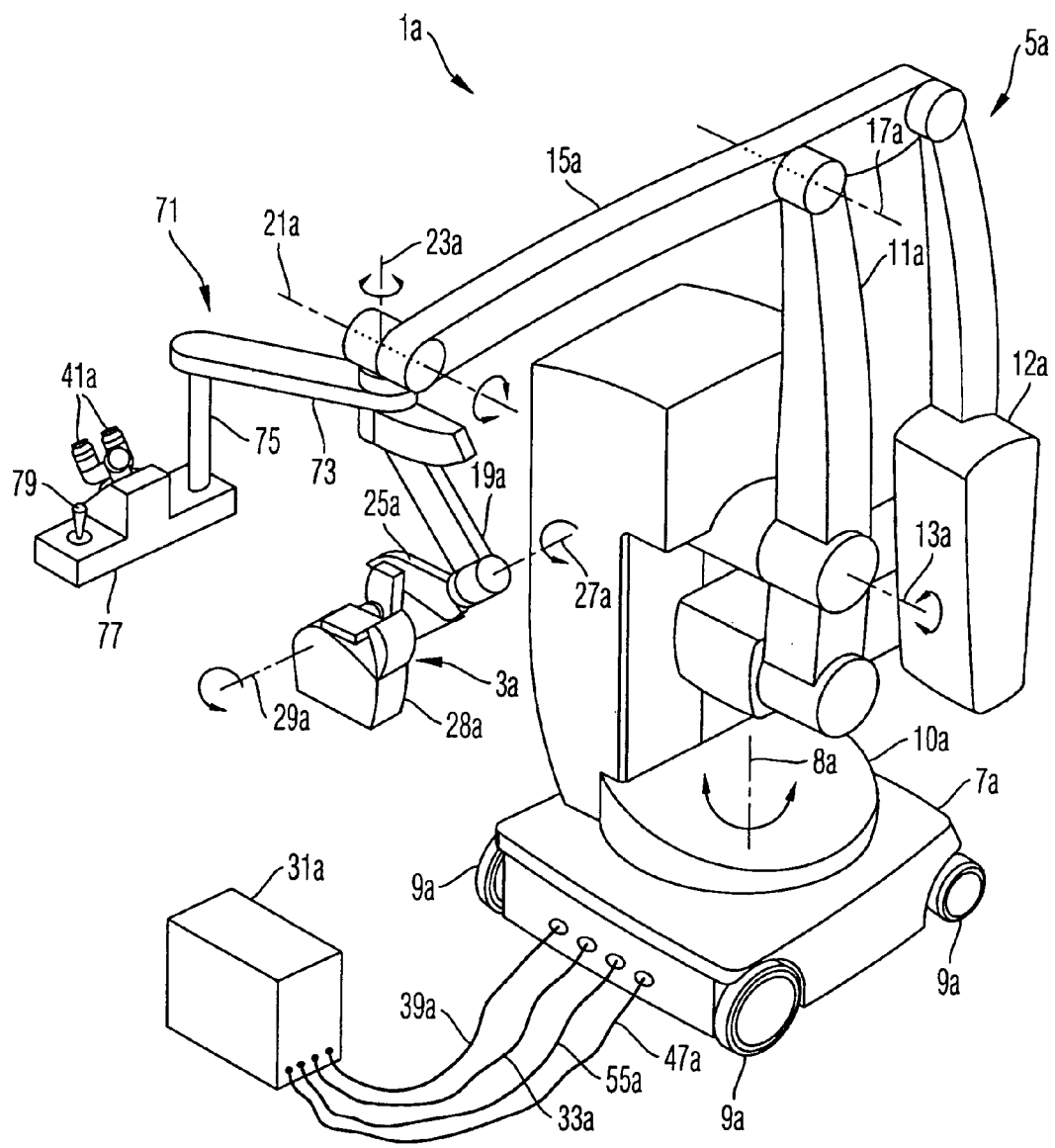
FIG. 2 is perspective illustration of an embodiment of a microscopy system having a visualizing unit which is separate from an objective arrangement and which is carried by a support.

A microscopy system 1*a* shown in FIG. 2 has a similar configuration to that shown in FIG. 1. The microscopy system 1*a* comprises a microscopy optics 3*a* having an objective arrangement (not shown in FIG. 2) contained in a chassis 28*a* which is mounted on a support 5*a* such that it is displaceable in space. The support 5*a* comprises plural support members 7*a*, 10*a*, 11*a*, 15*a*, 19*a*, 25*a* which are pivotable relative to each other about axis 12*a*, 13*a*, 17*a*, 21*a*, 27*a* and 29*a*, wherein actuators are associated with the various axis to control the support 5*a* in view of displacing the objective arrangement and chassis 28*a*.

A visualizing unit of the microscopy optics 3a comprises a pair of oculars 41a which are mounted on a support 71 comprising a horizontal arm 73 mounted on the support arm 15a of the support 5a to be rotatable about vertical axis 23a. A rod 75 carrying a desk 77 is suspended from the arm 73. The desk carries the oculars 41a in a height of the eyes of the user (not shown in FIG. 2). A display, such as a LCD display, is provided in each of the oculars 41a for displaying an image of the object and detected by the objective within chassis 28a.

The objective arrangement supplies the detected images as electronic image data by a data cable 39a to a controller 31a. The controller 31a processes the image data and supplies processed image data via a data cable 47a to the pair of oculars.

Figure 3:
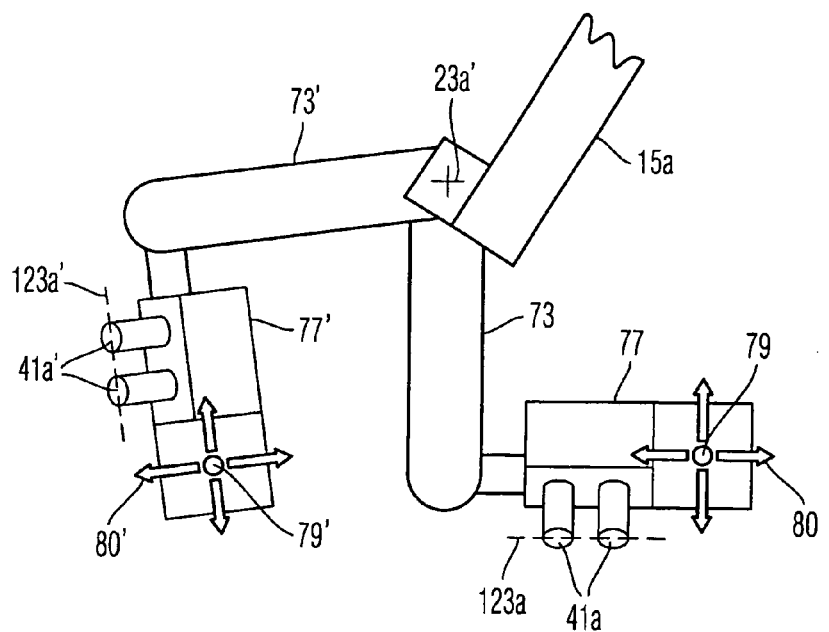
FIG. 3 is an elevational view of a portion of the microscopy system shown in FIG. 2.

Only one visualizing unit 41a mounted on support 71 is shown in FIG. 2. It is also possible that two or more visualizing units for plural users are provided on separate supports 71, which are also rotatable about the axis 23a. The elevational view of FIG. 3 illustrates two visualizing units 41a and 41a' mounted on support 73 and 73', respectively.

A control stick of joystick 79 is mounted on the desk 77. The joystick 79 may be actuated by the user from a neutral position in four directions which are orthogonal to each other to generate a horizontal displacement of the objective arrangement 28a by controlling the actuators associated with the respective pivoting axis of the support 5a. For this purpose a rotational sensor is provided between arm 73 and support arm 15a to detect a rotational position of the arm 73 relative to support arm 15a about vertical axis 23a. The controller 31a controls the actuators in dependence of the detected rotational position such that the objective arrangement is displaced in a same direction as the user displaces the joystick 79. In addition to the functions of this joystick shown in FIG. 3, which is the displacement from the neutral position into the four orthogonal directions, the joystick may comprise further features of operation, or additional control elements may be provided on the desk 77 to also change such as an orientation or vertical position of the chassis 28a in space under the control of controller 31a.

For example, operation of an additional control element such as a switch may result in a rotation of the chassis 28a together with the objective arrangement about axis 23a.

The image data which are displayed to the eyes of the user by displays, such as displays contained in the head mounted display 43 or the oculars 41a, may be obtained in various ways. To give an example, two cameras directed onto the object plane may be comprised in the objective arrangement contained in chassis 28, 28a. However, when the user 44 moves relative to object 37, a perspective under which the object is perceived by using the microscopy system should be adapted to such changing positions of the user relative to the object. For this purpose it is necessary to change a stereo base of the objective arrangement in dependence of a position of the user within their accessible space. Plural possibilities are conceivable in this respect.

Figure 4:
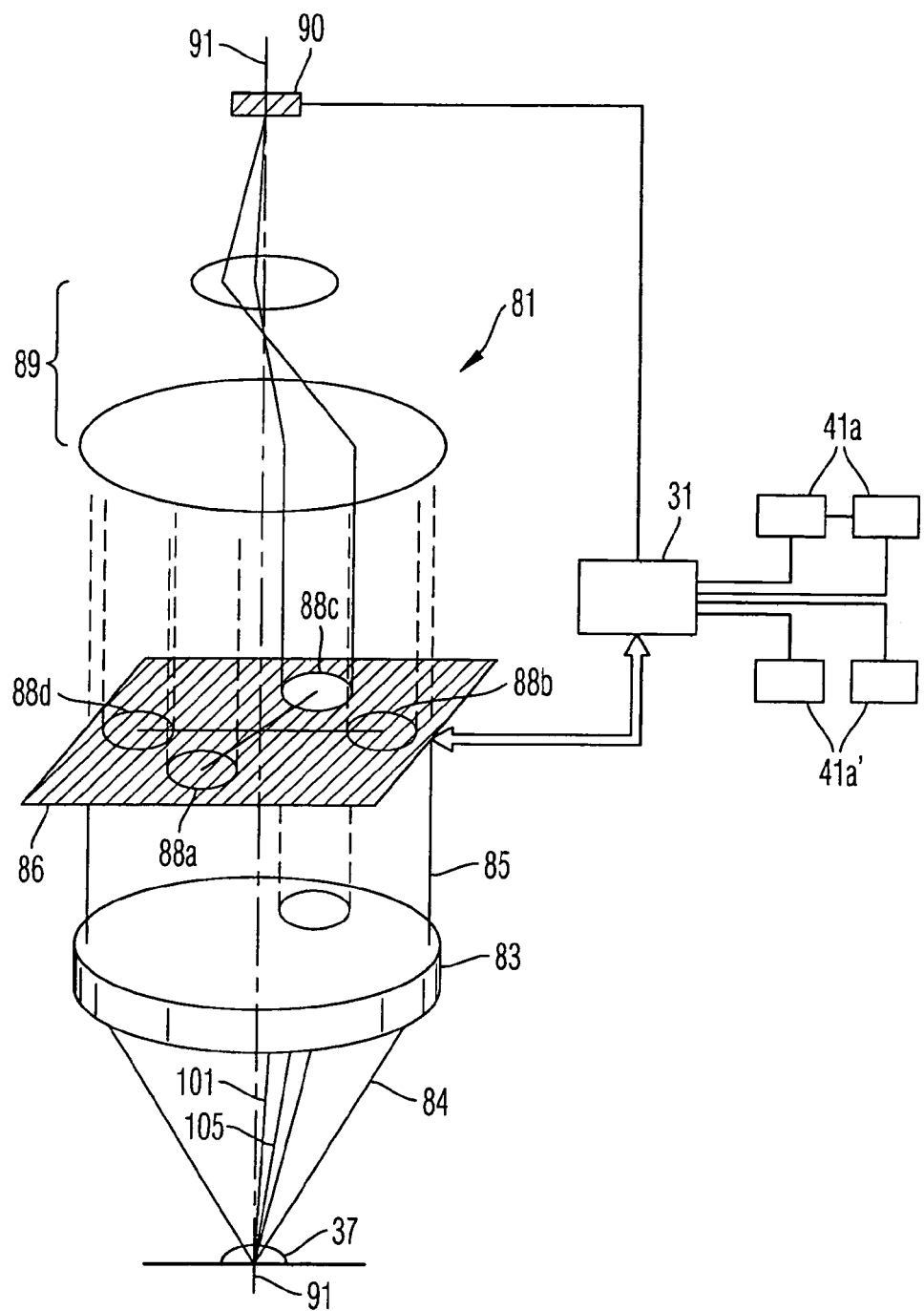
FIG. 4 is a schematic representation of a microscopy optics for generating a pair of stereoscopic images using a camera.

FIG. 4 schematically illustrates a function of an embodiment of an objective arrangement 81 contained in chassis 28. The objective arrangement 81 is provided for generating image data with at least one camera, and the image data are supplied to the oculars 41a, 41a' of FIG. 3 or to the head mounted display 43 of FIG. 1. For this purpose the objective arrangement 81 comprises a front lens group 83 transforming an object side bundle 84 of imaging rays into an image side bundle 85 of imaging rays. A beam shutter 86 is disposed within the image side bundle 85 of rays and comprises a plurality of liquid crystal light shutters which are controllable by the controller 31 to be switchable between a light transmitting state a light non transmitting state. FIG. 4 indicates four circular regions 88a, 88b, 88c, 88d of the beam shutter 86, wherein region 88d is associated with a left ocular 41a, region 88b is associated with the right ocular 41a, region 88a is associated with the right ocular 41a', and region 88c is associated with the left ocular 41a'. Only the liquid crystal elements within region 88c are in their light transmitting state, and all other liquid crystal elements are switched into their light non transmitting state. Accordingly, only those rays of bundle 85 traversing the shutter 86 in region 88c will be incident onto a camera 90 after traversing a camera adaptor optics 89. The image detected by camera 90 is read out by the controller 31 and supplied to the LCD display provided in the left ocular 41a'. Thereafter, the controller 31a controls the shutter 86 such that only the region 88a is light transmitting, and the image detected by camera 90 will be supplied to the display of the right ocular 41a'. By such a procedure, representations of the object from different viewing directions are visible in the left and right oculars 41a', respectively, such that the user viewing into the oculars 41a' will perceive a stereoscopic representation of object 37a.

Thereafter the controller 31a controls the shutter 86 such that only the region 88d is in the light transmitting state, and the detected image of the camera 90 will be supplied to the left ocular 41a. Thereafter, only region 88b will be switched to be light transmitting and the image detected by camera 90 will be supplied to the right ocular 41a. By such a procedure the oculars 41a will also display a stereoscopic representation of the object 37a.

A connecting line between centers of regions 88d and 88b may be referred to as a stereo base for the stereoscopic images supplied to visualizing unit 41a, and a connecting line between centers of regions 88a and 88c may be referred to as the stereo base for the stereoscopic images supplied to visualizing units 41a'. In particular, the orientations of the stereo bases may be parallel to orientations of a connecting line 123a, 123a' between the corresponding two oculars 41a, 41a' shown in FIG. 3.

When the user changes the rotational position of arm 73, 73' about axis 23a, the controller 31 will change the corresponding orientations of the stereo bases at the shutter 86, such that the regions 88a, . . . , 88d are displaced in a circumferential direction about an optical axis 91 of the objective arrangement. Thus, stereoscopic representations of the object will be displayed by the ocular 41a, 41a' with a correct viewing direction or orientation of the stereo bases which correspond to the position of the ocular about axis 23a.

More details and other embodiments of the apparatus similar to that shown in FIG. 4, for generating stereoscopic representations of the object are disclosed in European patent application with publication number EP 1 333 305 A2 and in corresponding U.S. patent application with publication number US 2004/0017607 A1 which documents are incorporated herein by reference.

According to a further embodiment, the image data supplied to the oculars as illustrated above will also be supplied to the head mounted display (reference numeral 43 in FIG. 1) such that the user will perceive a stereoscopic representation of the object with a correct stereo base, wherein the stereo base may be orientated in dependence of a position of the head, or any other body portion of the user, in a circumferential direction about the object.

A further embodiment of the invention, in which the stereo base is determined in dependence of an orientation of a body portion of the user, rather in dependence of a circumferential position of the user about the object, is illustrated with reference to FIG. 5 below.

Figure 5:
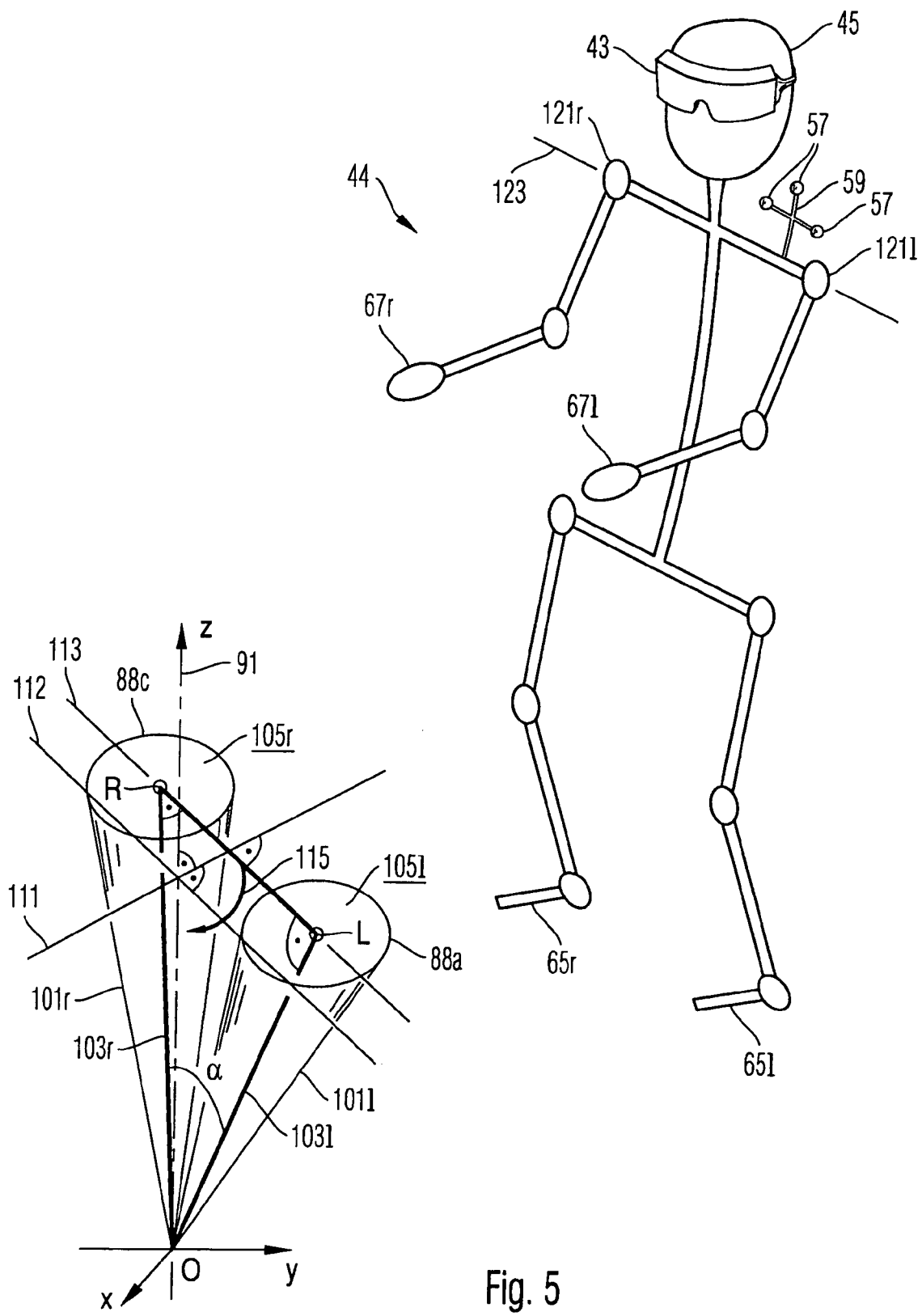
FIG. 5 is a diagram illustrating a function of the microscopy optics of FIG. 4.

FIG. 5 shows a coordinate system xyz having an origin O wherein an xy plane of the coordinate system coincides with an object plane of objective arrangement 81, and wherein a z axis of the coordinate system coincides with a main axis or optical axis 91 of the objective arrangement 81. FIG. 5 further shows imaging arrays 101*l* and 101*r* traversing regions 88*a* and 88*c*, respectively, shown in FIG. 4. Imaging ray bundles 101*l* and 101*r* represent beam paths which the camera 90 uses to detect images of the object, wherein representations of these images are provided to the left and right eyes of the user respectively. The two rays bundles 101*l* and 101*r* have central main rays 103*l* and 103*r*, respectively. These main central rays 103*l* and 103*r* determine the stereo base and intersect with each other at the origin O at an angle a which is referred to as the stereo angle. Reference numerals 105*l* and 105*r* in FIG. 5 indicate cross sections of the rays bundles 101*l* and 101*r* in a plane parallel to the object plane xy. The main central rays 103*l* and 103*r* intersect this plane at points L and R respectively. A line RL between the two points R and L represents the corresponding stereo base, and the points R, L and O define a common plane RLO.

Reference numerals 111 and 112 in FIG. 5 indicate two lines which are orthogonal to each other and which coincide with the plane of cross sections 105. Line 112 intersects with the z axis. Reference numeral 113 indicates a line coinciding with line RL. By controlling the beam shutter 86, the controller 31 of the microscopy system may change a distance between lines 112 and 113 and to change an orientation of lines 111, 112 and 113 within the plane of cross sections 105 about the z axis, as indicated by an arrow 115 in FIG. 5. Thus, also the plane RLO is displaced about the optical axis or main axis 91 of the objective arrangement under the control of controller 31.

FIG. 5 further shows a schematic skeleton model of the user with his head 45, left shoulder 121*l*, right shoulder 121*r*, left hand 67*l*, right hand 67*r*, left foot 65*l* and right foot 65*r*. A line traversing the left and right shoulders 121*l* and 121*r* is indicated with reference numeral 123.

The orientation of line RL about main axis 91 is adjusted under the control of controller 31 such that the plane RLO is oriented parallel with respect to line 123. In the situation shown in FIG. 5 where the main axis or optical axis 91 of the objective arrangement is oriented in the vertical direction which is also parallel to the main body axis of the user 45, the line RL is also parallel to line 123. In a more general situation where the objective arrangement may be arbitrarily disposed and oriented relative to the object, the main axis or optical axis of the objective arrangement arrangement will be not oriented along the vertical direction. In such situation the line RL will not always be oriented parallel to line 123. Still, the plane RLO may be oriented substantially parallel to line 123. Further, as already illustrated above, an offset angle may be provided between plane RLO and line 123.

The orientation of the two shoulders 121*l*, 121*r* and of the line 123 of the user, respectively, may be determined by fixing the mounting rods 59 of the three light emitting diodes 57 shown in FIG. 1 to one of the shoulders 121 of the user. The microscopy system 1 may then detect the orientation of the shoulders 121 by analyzing the images detected by cameras 53 for determining the orientation of plane RLO. Herein it is also possible to provide an offset between orientations of line 123 and the orientation of plane RLO for allowing the user to perform his task while maintaining his shoulders tilted with respect to the object when it is necessary for example to manipulate with his right arm a location of the object which is more distant from the body than a location manipulated with the left hand.

According to an alternative embodiment, the orientation of the plane RLO about the main axis 9 may be determined as follows: The location of the two shoulders 121*r*, 121*l* in space defines a vertical plane intersecting the two shoulders 121*r*, 121*l*. Such vertical plane is displaced in parallel such that it intersects with origin O. The plane RLO will then be displaced in circumferential direction about main axis 91 such that a line of intersection between the displaced vertical plane and the plane RLO coincides with the object plane xy.

Apart from the above illustrated procedures of geometrically determining the orientation of the plane RLO about the main axis, many other procedures of calculations are conceivable which will achieve similar results in practice.

Figure 6:
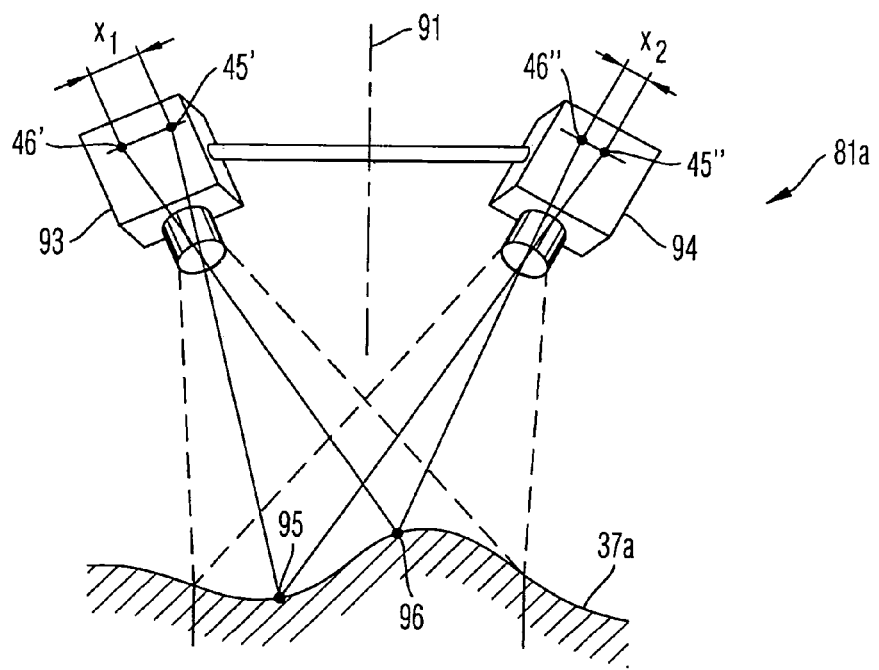
FIG. 6 is a schematic representation of a microscopy optics for generating a pair of stereoscopic images using a topology detector and a data model.

FIG. 6 shows a further embodiment of an objective arrangement which may be used in the microscopy system shown in FIGS. 1 and 2 for generating pairs of stereoscopic representations. The objective arrangement 81*a* disposed within chassis 28 comprises two cameras 93 and 94 which are disposed at a distance from each other and which detect images of an object 37*a*. It is apparent from FIG. 6 that different locations 95 and 96 of the object 37*a* are imaged to different locations 45', 46' and 45'', 46'', respectively, in the images detected by cameras 93 and 94. By analyzing the images detected by both cameras, the controller 31 may determine the topology of the object 37*a* and generate a corresponding data model. The data model is then used to generate the two representations which are supplied to the display of the visualizing unit. These representations are generated from the data model of the object such that the user looking at the display will perceive a stereoscopic representation of the object with a correct stereo base.

Figure 7:
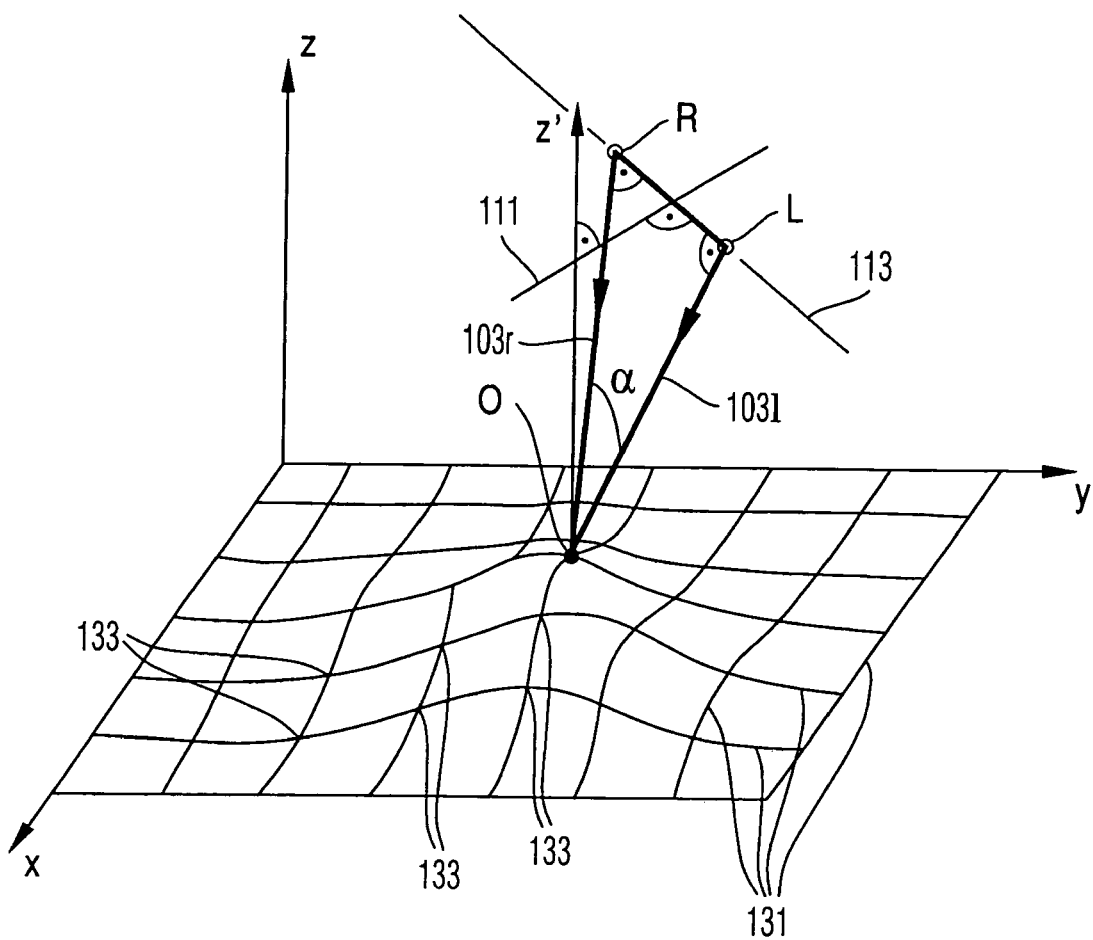
FIG. 7 is a diagram for illustration a function of the microscopy optics of FIG. 6.

FIG. 7 shows more details of the generation of the two representations from the data model.

The data model calculated from the images of the topology detector 81 is schematically illustrated as grid lines 131. Each intersection 133 of grid lines 131 is associated with a set of coordinates x, y, z of the corresponding points 133 of intersection. Thus, the three-dimensional data model may be represented as a plurality of triples of numbers representing coordinates of locations on the surface of the object. Herein, additional sets of data may be associated with a subset of the points 133 of intersection or with all points 133 of intersection. The additional sets of data may be indicative of additional properties of the object locations, such as a color of the respective locations.

An orientation and position of a main axis 91 of the topology detector 81 relative to the object 37 defines an orientation and position of an axis z' of the data model. The axis z' intersects the plane of grid lines 131 at a point O. It is not necessary that the axis z' is parallel to a main axis z of a xyz coordinate system in which the data model is calculated.

The pair of representations is calculated by the controller 31 from the data model such that the representations represent the object as if it was viewed from directions 103*l*, 103*r*, respectively. Herein, the viewing directions 103*l*, 103*r* extent towards each other and intersect each other at location O under an angle α which represents the stereo angle.

In a similar manner as it is illustrated above with reference to FIG. 5, points of origin R and L of arrows representing the directions 103*l* and 103*r*, respectively, may be determined, wherein the points of origin R, L are located in a plane orthogonal with respect to the z' axis which plane also coincides with a line 111 intersecting the z' axis and with a line 113 which connects locations R and L and which is orthogonal to line 111. The generation of the representations supplied to the display may be changed by changing a distance between the line 113 and the z' axis or by rotating the line RL about the z' axis, for changing the stereo base of the stereoscopic representation.

Similar to the embodiment shown in FIG. 5, the orientation of the line RL relative to the axis z' is determined in dependence of an orientation of a line 123 connecting the two shoulders 121*l*, 121*r*. Again, any body portion of the user other than the shoulder may be used for determining the stereo base of the generated representation of the object.

More details and other embodiments of the system for generating stereoscopic representations of the object as illustrated above with reference to FIGS. 6 and 7 are disclosed in European patent application with publication number EP 1 333 306 A2 and in corresponding U.S. patent application with publication number US 2003/0151810 A1 which documents are incorporated herein by reference.

Further, an orientation of the display rather than the body portion of the user may be used for determining the stereo base. For example, the line 123*a* indicated in FIG. 3 and connecting corresponding portions of the two oculars may be used for determining the orientation of the plane RLO in the xyz space. A corresponding line may be defined for the head mounted display carried on the head of the user for determining the orientation of the plane RLO.

Summarized a microscopy system and method provides functionalities for a user which are controllable by the user by displacing a body portion of the user. The functionalities comprise displacing a portion of a support mounting the microscopy optics and adjusting a stereo base for generating stereoscopic representations of an object.

The present invention has been described by way of exemplary embodiments to which it is not limited. Variations and modifications will occur to those skilled in the art without departing from the scope of the present invention as recited in the appended claims and equivalents thereof.

What is claimed is:

1. A microscopy system for displaying a representation of an object to at least one user, the system comprising:
   a microscopy optics having an objective arrangement for imaging the object to be disposed in a region of an object plane of the objective arrangement, and a visualizing unit for displaying a representation of the object to the user;
   a first support for mounting at least the objective arrangement of the microscopy optics relative to the object, wherein the first support comprises at least one actuator for displacing the objective arrangement relative to the object;
   a first position detector configured to detect a position of at least one of a body portion of the user and the visualizing unit relative to a predetermined location; and
   a control system comprising a first control portion configured to control the at least one actuator of the first support with respect to a displacement of the objective arrangement in dependence of a detected displacement of the at least one of the body portion of the user and the visualizing unit, and wherein the first control portion is further configured to control the at least one actuator such that an amount of the displacement of the objective arrangement is less than an amount of the detected position.

2. The microscopy system according to claim 1, wherein an imaging magnification of the microscopy optics is adjustable, and wherein a ratio between the amount of the detected displacement and the amount of the displacement of the objective arrangement is dependent on the adjusted magnification.

3. The microscopy system according to claim 1, wherein the first control portion of the control system is further configured to control the at least one actuator of the first support with respect to the displacement of the objective arrangement such that a direction of the displacement of the objective arrangement corresponds to a direction of the displacement of the at least one of the body portion of the user and the visualizing unit.

4. The microscopy system according to claim 1, wherein the displacements of the body portion of the user, the visualizing unit and the objective arrangement each comprise at least one of a translational movement and a rotational movement.

5. The microscopy system according to claim 1, further comprising an activation signal detector, which is different from the first position detector, for providing an activation signal upon operation by the user, wherein the first control portion of the control system is configured to control the at least one actuator of the first support with respect to the displacement of the objective arrangement only upon receipt of the activation signal.

6. The microscopy system according to claim 1, wherein the visualizing unit comprises at least one ocular, and wherein the objective arrangement and the at least one ocular have a common optical path.

7. The microscopy system according to claim 1, wherein the visualizing unit comprises at least one display which is separate from the objective arrangement and which is configured to display image data representing a representation of the object.

8. The microscopy system according to claim 7, wherein the visualizing unit comprises a head mounted display.

9. The microscopy system according to claim 1, further comprising a second support for mounting the visualizing unit such that the visualizing unit is displaceable relative to the objective arrangement.

10. The microscopy system according to claim 1, wherein the objective arrangement comprises at least one of a topography detector and a camera, for generating image data representing the representation of the object.

11. A microscopy system for displaying a representation of an object to at least one user, the system comprising:
   a microscopy optics having an objective arrangement for imaging the object to be disposed in a region of an object plane of the objective arrangement, and a visualizing unit for displaying a representation of the object to the user;
   a first support for mounting at least the objective arrangement of the microscopy optics close to the object, wherein the first support comprises at least one actuator for displacing the objective arrangement relative to the object;
   a first position detector configured to detect a position of at least one of a body portion of the user and the visualizing unit relative to a predetermined location;
   a control system comprising a first control portion configured to control the at least one actuator of the first support with respect to a displacement of the objective arrangement in dependence on a detected displacement of the at least one of the body portion of the user and the visualizing unit; and an activation signal detector, which is different from the first position detector, for providing an activation signal upon operation by the user;

wherein the first control portion of the control system is configured to control the at least one actuator of the first support with respect to the displacement of the objective arrangement only upon receipt of the activation signal;

wherein the visualizing unit comprises at least one display which is separate from the objective arrangement and which is configured to display image data representing a representation of the object: and wherein the visualizing unit comprises a head mounted display.

12. The microscopy system according to claim 11, further comprising a switch operable by the user for providing the activation signal.

13. The microscopy system according to claim 12, wherein the switch comprises at least one of a foot switch and a mouth switch.

14. The microscopy system according to claim 11, further comprising a microphone for receiving an acoustic signal generated by the user, wherein the control system comprises a second control portion providing the activation signal in dependence of an analysis of the detected acoustic signal.

15. The microscopy system according to claim 11, wherein the visualizing unit comprises at least one ocular, and wherein the objective arrangement and the at least one ocular have a common optical path.

16. The microscopy system according to claim 11, further comprising a second support for mounting the visualizing unit such that the visualizing unit is displaceable relative to the objective arrangement.

17. The microscopy system according to claim 11, wherein the objective arrangement comprises at least one of a topography detector and a camera, for generating image data representing the representation of the object.

18. A method of generating at least one pair of stereoscopic representations of an object, the method involving:
using a microscopy system, comprising an objective arrangement having a main axis, an object plane oriented transversely to the main axis and first and second beam paths, each beam path having a central ray, wherein the central rays intersect each other at a common location and coincide with a common first plane; and
using first and second displays for the first and second eyes of the user, respectively;
the method comprising:
detecting at least one of an orientation of a body portion of the user and an orientation of the first and second displays, relative to a first location; and then
adjusting an orientation of the first plane about the main axis in dependence of the detected orientation; and then
detecting at least one first image of the object plane through the first beam path and displaying a first representation of the object corresponding to the first image using the first display, and detecting at least one second image of the object plane through the second beam path and displaying a second representation of the object corresponding to the second image using the second display.

19. The method according to claim 18, wherein the detected orientation of the body portion of the user comprises at least one of an orientation of a head of the user and an orientation corresponding to an orientation of a line connecting left and right shoulders of the user.

20. A method of generating at least one pair of stereoscopic representations of an object, the method involving:
using a microscopy system having a topology detector for generating a data model representing a topology of the object, wherein the topology detector has a main axis;
using first and second displays for the first and second eyes of the user, respectively;
the method comprising:
detecting at least one of an orientation of a body portion of the user and an orientation of the pair of displays relative to a first location; and then
generating a first representation of the object from the data model generated by the topology detector and displaying the first representation of the object using the first display, and generating a second representation of the object from the data model generated by the topology detector and displaying the second representation of the object using the second display;
wherein the first representation of the object and the second representation of the object correspond to images of the object from different viewing directions defining a substantially common first plane, and wherein an orientation of the first plane about an axis associated with the object and which is transversely oriented to the viewing directions is determined in dependence of the at least one detected orientation.

21. The method according to claim 20, wherein the detected orientation of the body portion of the user comprises at least one of an orientation of a head of the user and an orientation corresponding to an orientation of a line connecting left and right shoulders of the user.

22. A microscopy system for displaying a stereoscopic representation of an object to at least one user, the system comprising:
an objective arrangement having a main axis, an object plane oriented transversely to the main axis and at least first and second beam paths, each beam path defining a central ray, wherein the central rays intersect each other at substantially a common location and coincide with a common first plane;
a first display for displaying a first representation of the object corresponding to a first image detected through the first beam path, and a second display for displaying a second representation of the object corresponding to a second image detected through the second beam path;
an orientation detector configured for detecting at least one of an orientation of a body portion of the user and an orientation of the first display and an orientation of second display, relative to a first location;
a control system having a first control portion configured to adjust an orientation of the first plane of the objective arrangement about the main axis of the objective arrangement in dependence of the orientation detected by the orientation detector.

23. The microscopy system according to claim 22, wherein the first and second displays are included in a head mounted display.

24. The microscopy system according to claim 22, further comprising:
a first support mounting at least the objective arrangement of the microscopy optics relative to the object, wherein the first support comprises at least one actuator for displacing the objective arrangement relative to the object; and a first position detector configured to detect a position of at least one of a body portion of the user, the first display and the second display, relative to a predetermined location;

wherein the control system further comprises a second control portion configured to control the at least one actuator of the first support with respect to a displacement of the objective arrangement in dependence of a detected displacement the at least one of the body portion of the user, the first display and the second display.

25. The microscopy system according to claim 24, wherein the second control portion is further configured to control the at least one actuator such that an amount of the displacement of the objective arrangement is less than an amount of the detected displacement.

26. The microscopy system according to claim 22, further comprising a second support mounting the first and second displays.

27. The microscopy system according to claim 22, further comprising:

a first support mounting at least the objective arrangement of the microscopy optics relative to the object; and a second support mounting the first and second displays;

wherein the first support comprises a plurality of support members hinged to each other, wherein the plurality of support members comprises a base member configured to be fixedly mounted relative to the object, and a distal end member carrying the objective arrangement, and wherein one of the support members which is different from the base member carries the second support.

28. A microscopy system for displaying a stereoscopic representation of an object to at least one user, the system comprising:

a topology detector for generating a data model representing a topology of the object, wherein the topology detector has a main axis;

a first display for displaying a first representation of the object, and a second display for displaying a second representation of the object;

an orientation detector configured for detecting at least one of an orientation of a body portion of the user, an orientation of the first display and an orientation of the second display, relative to a first location;

a control system having a first control portion configured to generate the first representation of the object from the data model generated by the topology detector, and to generate a second representation of the object from the data model generated by the topology detector;

wherein the first representation and the second representation correspond to images of the object from different viewing directions defining a substantially common first plane, and wherein the first control portion is further configured to determine an orientation of the first plane about an axis associated with the object and which is transversely oriented to the viewing directions in dependence of the at least one detected orientation.

29. The microscopy system according to claim 28, wherein the first and second displays are included in a head mounted display.

30. The microscopy system according to claim 28, further comprising:

a first support mounting at least the topology detector relative to the object, wherein the first support comprises at least one actuator for displacing the topology detector relative to the object;

a first position detector configured to detect a position of at least one of a body portion of the user, the first display and the second display, relative to a predetermined location; and a control system comprising a second control portion configured to control the at least one actuator of the first support with respect to a displacement of the topology detector in dependence of a detected displacement of the at least one of the body portion of the user, the first display and the second display.

31. The microscopy system according to claim 30, wherein the second control portion is further configured to control the at least one actuator such that an amount of the displacement of the topology detector is less than an amount of the detected displacement.

32. The microscopy system according to claim 28, further comprising a second support mounting the first and second displays.

33. The microscopy system according to claim 28, further comprising:

a first support mounting at least the topology detector relative to the object; and a second support mounting the first and second displays;

wherein the first support comprises a plurality of support members hinged to each other, wherein the plurality of support members comprises a base member configured to be fixedly mounted relative to the object, and a distal end member carrying the topology detector, and wherein one of the support members which is different from the base member carries the second support.

* * * * *